United States Patent [19]
Wilson et al.

[11] Patent Number: 5,943,633
[45] Date of Patent: Aug. 24, 1999

[54] AUTOMATIC INFUSION PUMP TESTER

[75] Inventors: Larry Wilson, Poway, Calif.; Thomas H. Burdick, Deerfield; Sho Chen, Northfield, both of Ill.

[73] Assignee: Sabratek Corporation, Niles, Ill.

[21] Appl. No.: 08/583,468

[22] Filed: Jan. 5, 1996

[51] Int. Cl.[6] .................................................. G01F 25/00
[52] U.S. Cl. ............................................. 702/45; 604/67
[58] Field of Search ................................. 364/509, 510; 417/18, 43, 63; 604/51, 67; 702/45

[56] References Cited

U.S. PATENT DOCUMENTS

| | | | |
|---|---|---|---|
| 4,756,706 | 7/1988 | Kerns et al. | 604/66 |
| 5,006,997 | 4/1991 | Reich | 364/510 |
| 5,116,312 | 5/1992 | Blankenship et al. | 604/66 |
| 5,244,463 | 9/1993 | Cordner, Jr. et al. | 604/131 |
| 5,272,917 | 12/1993 | Pippert | 73/168 |
| 5,298,021 | 3/1994 | Sherer | 604/66 |
| 5,669,877 | 9/1997 | Blomquist | 604/67 |

FOREIGN PATENT DOCUMENTS

| | | |
|---|---|---|
| 40 00 873 C1 | 7/1991 | Germany . |
| 41 00 317 A1 | 7/1992 | Germany . |
| 42 20 831 C1 | 4/1994 | Germany . |

OTHER PUBLICATIONS

Bio–Tek Instruments, Inc., Biomedical Catalog #18, Apr. 1994, 7 pages.

Dynatech Nevada, Biomedical Test and Clinical Training Systems Product Catalog, vol. 29, 4 pages, 1994.

Spectrel Medical, Certamatic Recertification System brochure, 24 pages date unknown.

Datrend Systems Inc., Infutest 2000 flier, 4 pages date unknown.

Primary Examiner—James P. Trammell
Assistant Examiner—Matthew Smithers
Attorney, Agent, or Firm—Fitch, Even, Tabin & Flannery

[57] ABSTRACT

An apparatus for automatically testing an infusion pump is provided with a pump tester adapted to be coupled to an infusion pump for performing a plurality of tests on the pump. The pump tester performs a first type of test on the pump and a second type of test on the pump. The testing apparatus automatically causes the infusion pump to undergo an operation sequence in which the infusion pump pumps liquid during the performance of at least one of the tests. Whereas the normal operation of the infusion pump is controlled by an infusion pump input device which is capable of generating a plurality of electronic signals in response to manual activation of the input device by a user, the pump tester automatically causes the infusion pump to undergo its operation during testing may include generating a plurality of testing commands. Each of the pump tester testing commands emulates one of the electronic signals which the infusion pump input device is capable of generating, and the pump tester transmits the testing commands to the infusion pump under test.

3 Claims, 11 Drawing Sheets

| INFUSION PUMP RECERTIFICATION RECORD | | | |
|---|---|---|---|
| PUMP TYPE | PUMP S/N: | SOFTWARE VER: | TEST DATE: |
| SABRATEK 3030 | 9125 | 1E.1.00 | 08/29/95 |

OPERATOR: CHEN

TEST RESULTS

| | | |
|---|---|---|
| DELIVER VOLUME (ml) | 14.15 | FAIL |
| LOW PRESSURE (psi) | 7.82 | PASS |
| HIGH PRESSURE (psi) | 19.14 | PASS |
| CUSTOMER PRESSURE (psi) | | |
| LEAKAGE CURRENT (μA) | 29.55 | PASS |
| GROUND RESISTANCE (ohm) | 0.11 | PASS |
| DOOR SWITCH | PASS | PASS |
| AIR-IN-LINE | PASS | PASS |
| UP OCCLUSION FUNCTION (6060) | | |
| BOLUS FUNCTION (6060) | | |

DATA SAVE TO: \ c:\logsave

SAVE/EXIT

EXIT

AUTOMATIC INFUSION PUMP TESTER

BACKGROUND OF THE INVENTION

The invention is directed to an automatic infusion pump testing apparatus for performing a number of tests on an infusion pump to determine whether the pump is operating correctly.

An infusion pump is used to automatically administer liquid medicant to a patient. The liquid medicant is supplied from a source of medicant and pumped into the patient via a catheter or other injection device. The manner in which the liquid is infused is controlled by the infusion pump, which may have various modes of infusion, such as a continuous mode in which the liquid medicant is continuously infused at a constant rate, or a ramp mode in which the rate of infusion gradually increases, then remains constant, and then gradually decreases.

Infusion pumps must be periodically tested to determine whether they are functioning properly. Typically an infusion pump is tested by connecting the pump to some type of testing apparatus and then manually causing the pump to operate by pumping liquid. The pump operation is typically initiated by a test operator by manually activating an input device, such as a keypad, associated with the infusion pump. The need to have a test operator present during the test procedure to manually operate the infusion pump increases the cost of testing infusion pumps, particularly where a relatively large number are tested, and the work performed by a test operator is tedious.

SUMMARY OF THE INVENTION

The invention is directed to an apparatus for automatically testing an infusion pump. The testing apparatus has a pump tester adapted to be coupled to an infusion pump for performing a plurality of tests on the pump. The pump tester includes means for performing a first type of test on the pump and means for performing a second type of test on the pump. The testing apparatus has means for automatically causing the infusion pump to undergo an operation sequence in which the infusion pump pumps liquid during the performance of at least one of the tests.

Where the normal operation of the infusion pump is controlled by an infusion pump input device which is capable of generating a plurality of electronic signals in response to manual activation of the input device by a user, the means for automatically causing the infusion pump to undergo operation during testing may include means for generating a plurality of testing commands, each of which emulates one of the electronic signals which the infusion pump input device is capable of generating, and means for transmitting the testing commands to the infusion pump.

The pump tester may include means for performing a volume accuracy test on the infusion pump, means for performing an upstream occlusion test on the infusion pump, and means for performing a downstream occlusion test on the infusion pump.

The means for performing the volume accuracy test may have a liquid container into which a quantity of liquid is pumped during the operation sequence of the infusion pump and means for determining the volume of the quantity of liquid.

The means for performing the upstream occlusion test may have a valve coupled to a conduit connected upstream of the infusion pump for selectively interrupting the flow of the liquid through the conduit and means for determining whether the infusion pump generates an upstream occlusion signal in response to an interruption of liquid flow through the conduit.

The means for performing the downstream occlusion test may include a pressure sensor for generating a signal relating to the pressure of the liquid within a conduit connected downstream of the infusion pump and means for determining whether the infusion pump generates a downstream occlusion signal in response to an interruption of liquid flow through the conduit. The means for performing the downstream occlusion test may also include means for determining whether the liquid pressure is within a given range upon the detection a downstream occlusion by the infusion pump.

These and other features and advantages of the present invention will be apparent to those of ordinary skill in the art in view of the detailed description of the preferred embodiment, which is made with reference to the drawings, a brief description of which is provided below.

DETAILED DESCRIPTION OF A PREFERRED EMBODIMENT

Figure 1:
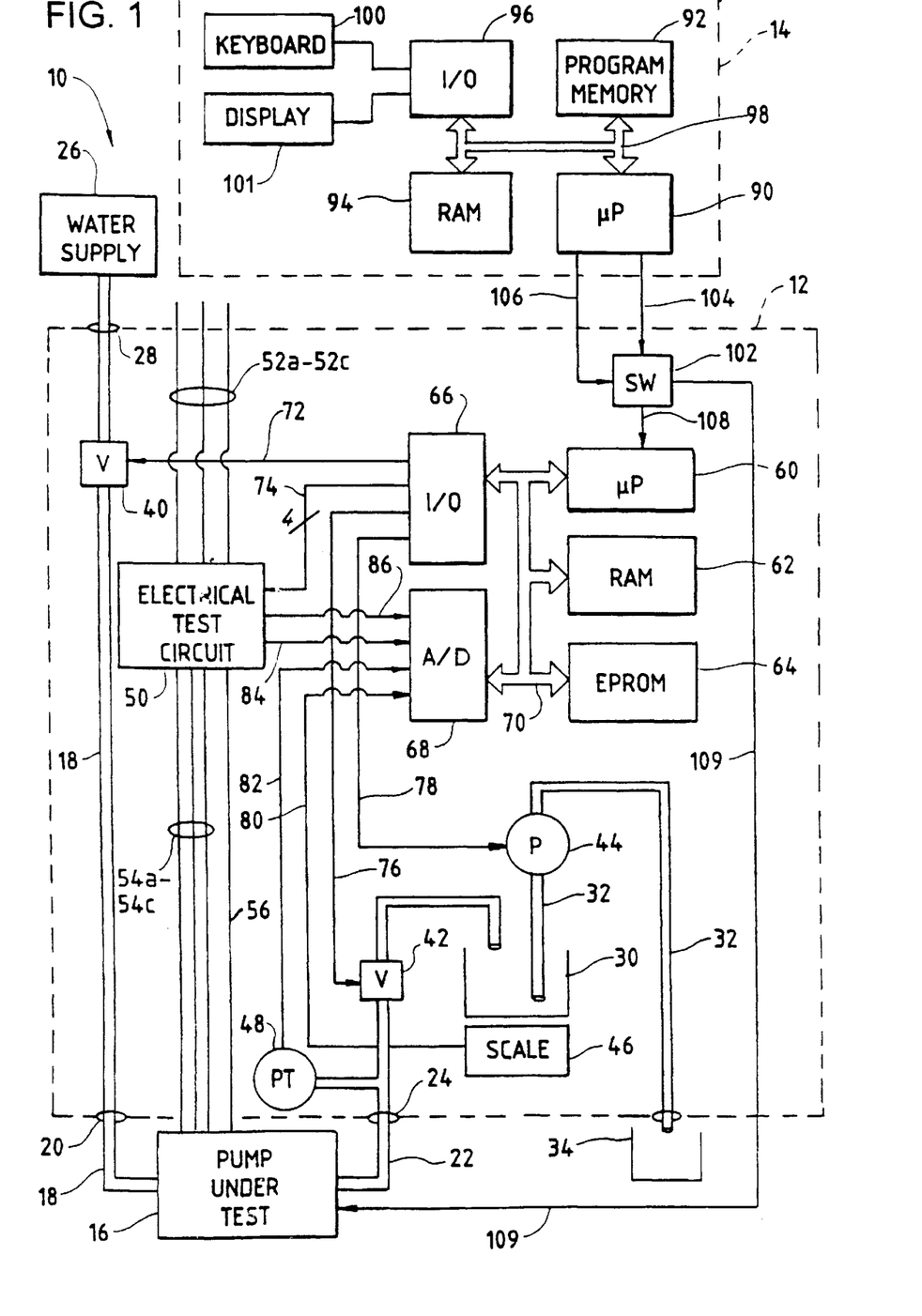
FIG. 1 is a block diagram of a preferred embodiment of an infusion pump testing apparatus in accordance with the invention shown connected to an infusion pump being tested.

A block diagram of a preferred embodiment of a pump testing apparatus 10 in accordance with the invention is shown in FIG. 1. The testing apparatus 10 includes a pump tester 12 and a computer 14 for controlling the pump tester 12.

An infusion pump 16 to be tested is hydraulically connected to the pump tester 12 via an upstream liquid conduit 18 connected to the pump tester 12 at a connection point schematically shown at 20 and a downstream liquid conduit 22 connected to the pump tester 12 at a connection point schematically shown at 24. Testing liquid, such as water, is supplied to the upstream liquid conduit 18 via a liquid source 26 hydraulically connected to the pump tester 12 at a connection point schematically shown at 28. The downstream liquid conduit 22 empties into a liquid container schematically shown at 30, and liquid may be pumped out of the container 30 via a liquid disposal conduit 32 which empties into a drain 34.

The water supply 26 is positioned at a height higher than that of the pump 16 so that water is provided to the pump 16 via the upstream conduit 18 under the influence of gravity. The flow of water into the infusion pump 16 may be interrupted by an on/off valve 40 connected to the upstream conduit 18, and the flow of water out of the infusion pump 16 may be interrupted by an on/off valve 42 connected to the downstream conduit 22. Water may be removed from the container 30 through the disposal conduit 32 via a pump 44. A scale 46, which may comprise a strain gauge that generates a signal proportional to weight, is provided to weigh the liquid container 30 and its contents, and a pressure transducer 48 is connected to the downstream conduit 22.

The pump tester 12 has an electrical test circuit 50 which is connected to a three-wire power line having three conductors 52a–52c. The test circuit 50 is connected to the infusion pump 16 via three power conductors 54a–54c and a separate ground line 56. The pump tester 12 includes a conventional microcontroller which is composed of a microprocessor 60, a random-access memory (RAM) 62, an electrically programmable read-only memory (EPROM) 64, and an I/O circuit 66 which is connected to an analog-to-digital (A/D) converter 68. The components 60–66 of the microcontroller and the A/D converter 68 are interconnected via an address/data bus 70.

The I/O circuit 66 has seven output lines 72–78, one which is connected to control the upstream valve 40, four of which are connected to the test circuit 50, one of which is connected to control the downstream valve 42, and one which is connected to control the discharge pump 44. The A/D converter 68 has four input lines 80–86, two of which are connected to the test circuit 50, one of which is connected to the pressure transducer 48, and one of which is connected to the scale 46.

The computer 14, which may be a conventional personal computer, includes a microprocessor 90, a program memory 92, such as disk memory or a ROM, a RAM 94, and an I/O circuit 96, all of which are interconnected via an address/data bus 98. The I/O circuit 96 is connected to a keyboard 100 and a visual display generator 101, such as a cathode ray tube (CRT).

The microprocessor 90 of the computer 14 is connected to a switch 102 in the pump tester 12 via a serial communications line 104, such as an RS-232 communications line, and a switch control line 106. The switch 102 is connected to the microprocessor 60 of the pump tester 12 via a serial communications line 108 and to the infusion pump 16 via a serial communications line 109. Based on the state of the switch control line 106, the computer 14 can communicate with either the pump tester 12 via the communications line 108 or with the infusion pump 16 via the communications line 109.

The overall operation of the testing apparatus 10 is controlled by a computer program stored in the program memory 92 and executed by the microprocessor 90, as described in detail below. However, the testing apparatus 10 could be designed so that the computer program is stored in the memory 64 and executed by the microprocessor 60 of the pump tester 12, thereby eliminating the need for the computer 14. Since the operation of the testing apparatus 10 is somewhat dependent upon the manner in which the infusion pump being tested operates, the operation of one type of infusion pump which may be tested by the testing apparatus 10 is described below. It should be appreciated, however, that the testing apparatus 10 could be used to test infusion pumps having different designs.

The Infusion Pump Being Tested

Figure 2:
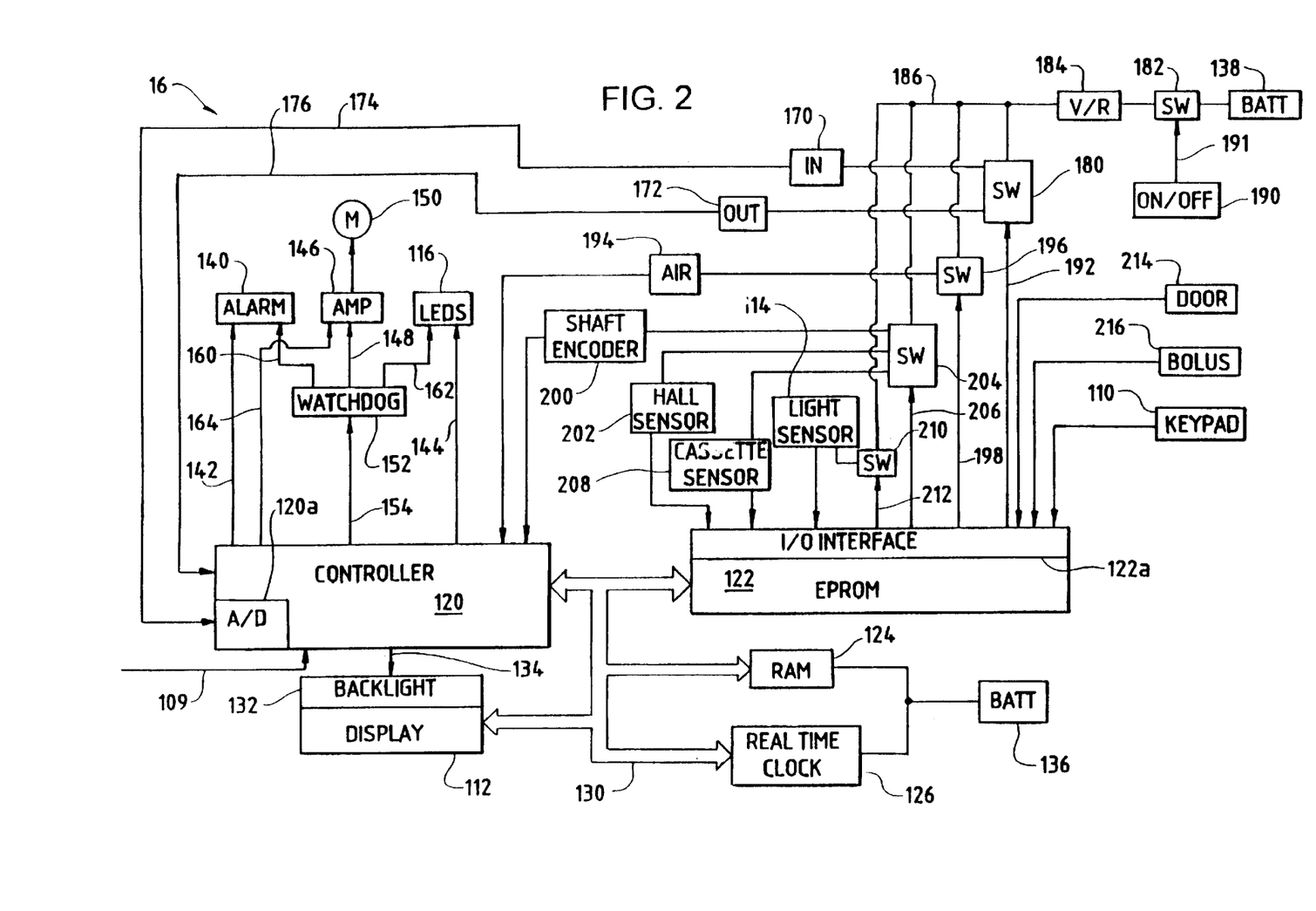
FIG. 2 is a block diagram of one embodiment of an infusion pump which can be tested by the testing apparatus.

A block diagram of the infusion pump 16 is illustrated in FIG. 2. Referring to FIG. 2, the infusion pump 16 has a keypad 110 via which a user may input data and commands, a selectively backlighted, dot matrix display 112 for displaying textual messages to the user, a light sensor 114 for detecting the level of ambient light, and a pair of light-emitting diodes (LED) 116, a green LED for indicating the normal operation of the pump 16 and a red LED for indicating an alarm or abnormal operating condition of the pump 16.

The infusion pump 16 includes a controller 120 with a built-in A/D converter 120a, an EPROM 122 having a built-in I/O interface 122a, a RAM 124, a real-time clock 126, all of which are interconnected by a communications bus 130. The display 112 has a backlight 132 which is selectively activated by an enable signal generated on a line 134 interconnecting the controller 120 and the backlight 132. Both the RAM 124 and the real-time clock 126 are connected to a battery 136 which supplies power to them only in the absence of system power (generated by a second battery 138). Since it is always powered, the RAM 124 is a non-volatile memory.

The controller 120 controls an audible alarm generator 140 via a line 142, the LEDs 116 via a line 144, and an amplifier circuit 146 via a line 148. The amplifier circuit 146 is connected to drive a pump motor 150 connected to a rotary pump wheel (not shown) which pumps liquid from the upstream conduit 18 to the downstream conduit 22.

During normal operation, the controller 120 sends a periodic signal to a watchdog timer 152 via a line 154. If the controller 120 should fail to transmit the periodic signal to the watchdog timer 152, which would indicate failure or malfunction of the controller 120, the watchdog timer 152 transmits a signal via a line 160 to cause the alarm 140 to sound, transmits a signal via a line 162 to cause the red LED to be illuminated, and transmits a signal via a line 148 to the amplifier circuit 146 to cause the pump motor 150 to stop.

The infusion pump 16 has a number of sensors which sense various conditions relating to the operation of the pump. These sensors include an input pressure sensor 170 for generating a signal indicative of the liquid pressure upstream of the pump 16 and an output pressure sensor 172 for generating a signal indicative of the liquid pressure downstream of the pump 16. The input pressure sensor 170 generates an analog signal, indicative of the upstream pressure, which is transmitted to the A/D converter 120a via a line 174, and the output pressure sensor 172 generates an analog signal, indicative of the downstream pressure, which is transmitted to the A/D converter 120a via a line 176. Each of the pressure sensors 170, 172, which are used to detect upstream and downstream occlusions, may be provided in the form of a strain gauge or beam (not shown) which is in contact with the exterior of the flexible tube (not shown) which passes through the pump 16 and which fluidly interconnects the conduits 18, 22 and a high-gain amplifier (not shown) connected to the strain beam.

The pressure sensors 170, 172 are connected to and receive power from a power switch 180 which is connected to the battery 138 through a system power switch 182, a voltage regulator 184, and a system power line 186. The system power switch 182 selectively supplies power from the battery 138 to the voltage regulator 184 based on the state of a pump on/off switch 190 connected to the system power switch 182 via a line 191. The power switch 180 is controlled by the controller 120 via the bus 130, the I/O interface 122a, and a line 192 which interconnects the I/O interface 122a and the power switch 180.

The pump 16 has an air-in-line sensor 194, which may be provided in the form of a conventional piezoelectric transmitter and receiver (not shown) coupled to a sensing circuit (not shown), to detect the presence of any significant air bubbles in the flexible tube within the pump. The air-in-line sensor 194 receives power from a power switch 196 which is connected to the system power line 186 and controlled by the controller 120 via a line 198 connected to the I/O interface 122a.

The pump 16 has a shaft encoder sensor 200 and a Hall-effect sensor 202 which receive power from a power switch 204 coupled to the system power line 186 and controlled by the controller 120 via a line 206. The shaft encoder sensor 200, which is disposed on the shaft of the motor 150, may be a two-phase motion sensing encoder which provides two signal outputs to the controller 120. The rotational speed of the motor 150 and its direction of rotation are determined by the controller 120 based upon the rate and phase relationship between the two signal outputs. The Hall-effect sensor 202 is disposed adjacent the rotary pump wheel (not shown) and detects magnetic encoding on the pump wheel for detecting rotation of the wheel.

A cassette sensor 208, which is connected to the power switch 204, detects the type of cassette which is inserted into the pump 16. The ambient light sensor 114 is connected to a power switch 210 which is controlled by the controller 120 via a line 212 from the I/O interface 122a. Signals generated by a door-open sensor 214, a bolus infusion request switch 216, and the keypad 110 are transmitted to the controller 120 via the I/O interface 122a. Although not shown in FIG. 2 for purposes of simplicity, the controller 120, the EPROM 122, the RAM 124 and the display 112 are also connected to and receive power from the system power line 186.

The operation of the infusion pump 16 is controlled by a computer program stored in the EPROM 122 and executed by the controller 120. A flowchart of the overall operation is illustrated in FIG. 3.

The infusion pump 16 has five basic modes of infusion: 1) a continuous mode in which the pump delivers a single volume at a single rate; 2) an auto-ramp mode in which the pump delivers liquid at a rate that gradually increases to a threshold rate, stays constant at the threshold rate, and then gradually decreases; 3) an intermittent mode in which the pump delivers discrete liquid volumes spaced over relatively long periods of time, such as a liquid volume every three hours; 4) a custom mode in which the pump can be programmed to deliver a unique infusion rate during each of 25 different time periods; and 5) a pain-controlled analgesic (PCA) mode during which the pump will periodically infuse boluses of analgesic in response to periodic requests by the patient, which requests are made via the bolus-request key 216.

Figure 3:
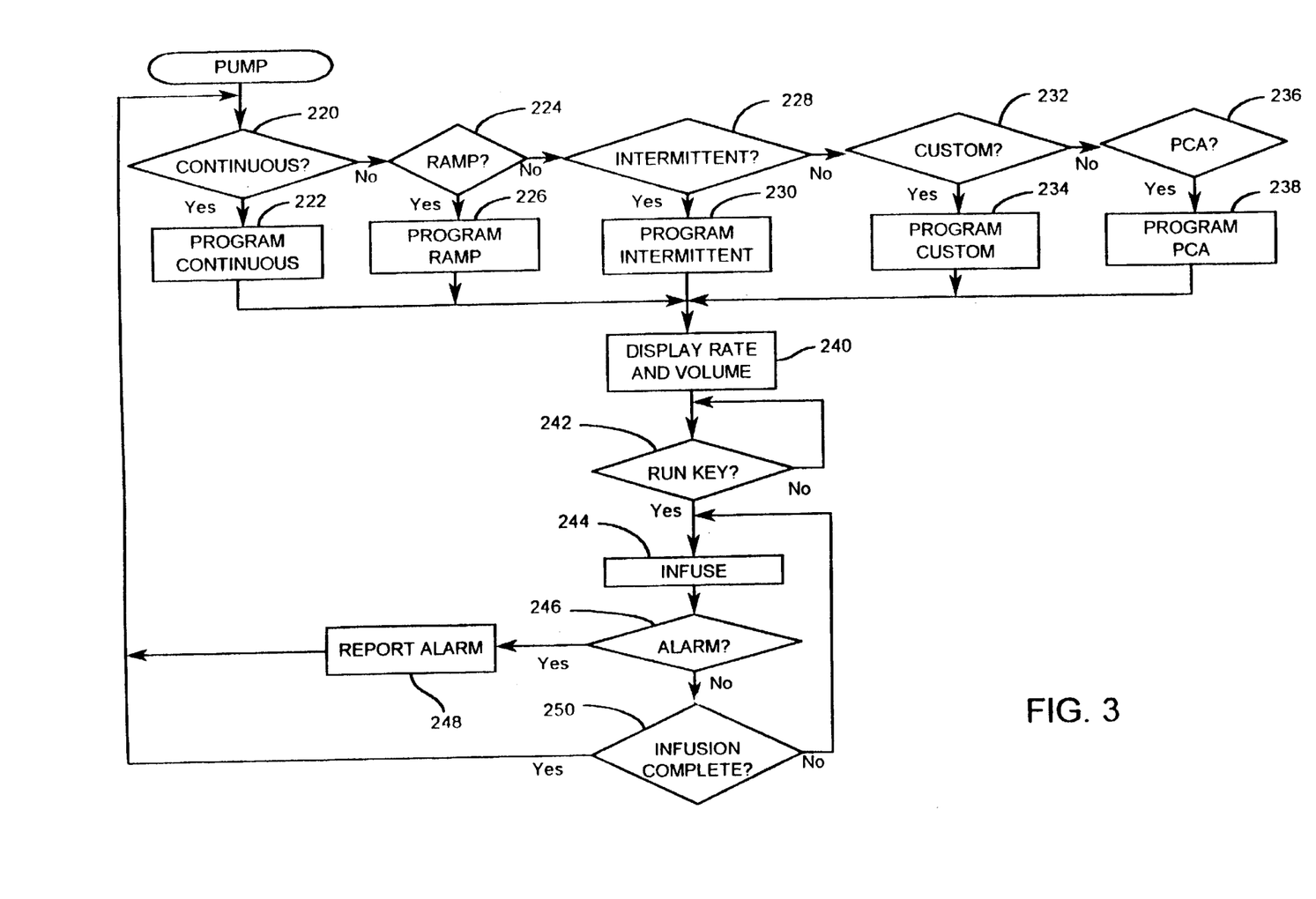
FIG. 3 is a flowchart of the operation of the infusion pump of FIG. 2.

Referring to FIG. 3, at step 220, the pump 16 generates on the display 112 the prompt "Continuous?" to the user. If the user desires to use the pump in its continuous mode, the user answers "yes" via the keypad 110, and the program branches to step 222 at which the continuous mode is programmed by the user by entering a number of infusion parameters, such as the desired infusion rate and the volume to be infused. At step 220, if the user does not want to use the continuous mode, the user answers "No," and the program branches to step 224. Steps 224–238 are generally the same as steps 220 and 222, except that the user may be prompted for different infusion parameters, depending on which of the five possible infusion modes is selected.

After the completion of one of the steps 222, 226, 230, 234, or 238, the program branches to step 240, at which point the infusion rate and the volume to be infused which were entered during one of the programming steps 222, 226, 230, 234, 238, are shown on the display 112. Then the program waits at step 242 until the "Run" key of the keypad 110 is pressed, at which point the program branches to step 244 where the pump 16 pumps liquid from the upstream conduit 18 to the downstream conduit 22 in accordance with the infusion mode selected at one of steps 220, 224, 228, 232, 236 and the infusion parameters entered at one of steps 222, 226, 230, 234, 238. If during the infusion an alarm is detected at step 246, such as an upstream occlusion alarm or a downstream occlusion alarm, the program branches to step 248 where an alarm message is displayed on the display 112. When the infusion is complete, as determined at step 250, the program branches back to step 220.

Operation of Pump Testing Apparatus

Figure 4:
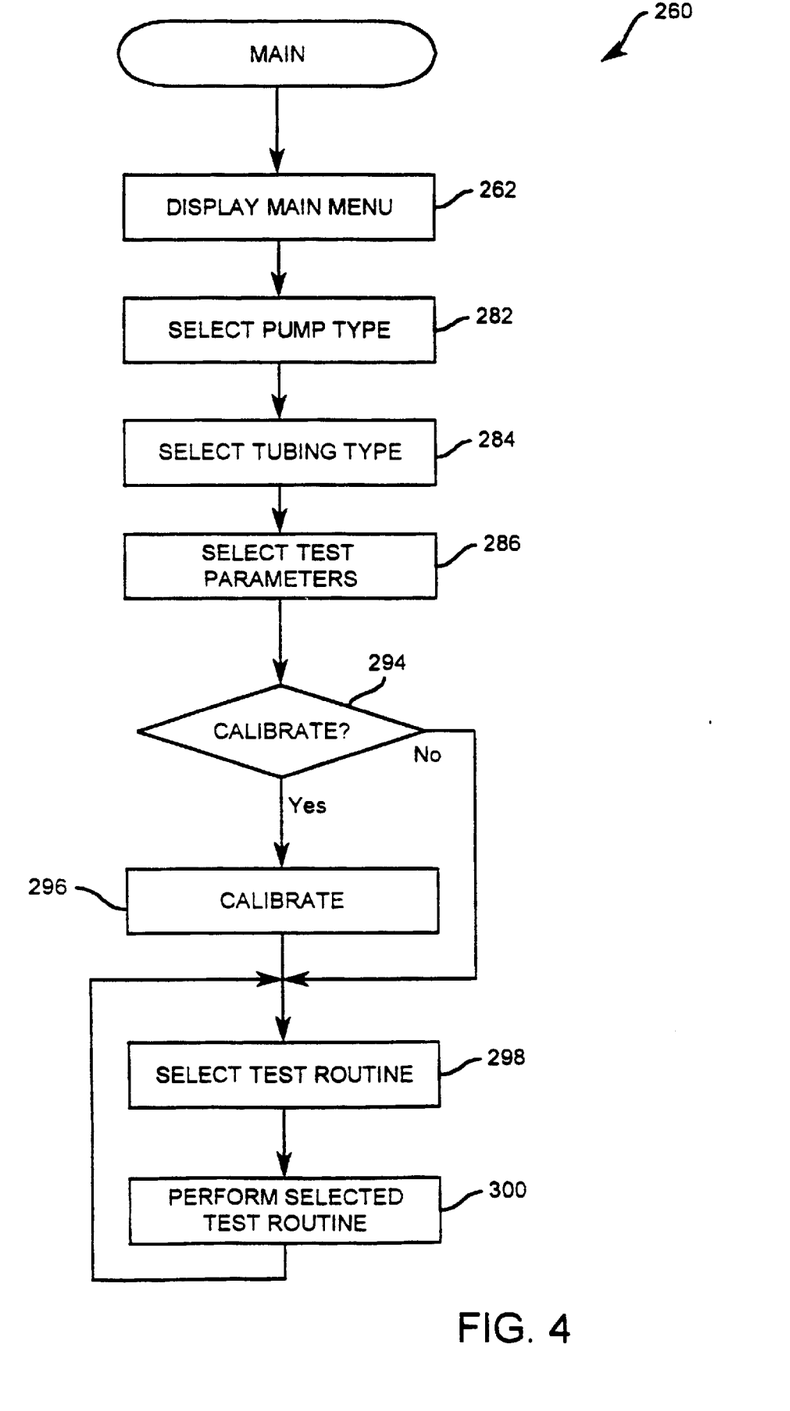
FIG. 4 is a flowchart of the operation of the pump testing apparatus of FIG. 1.
Figure 5:
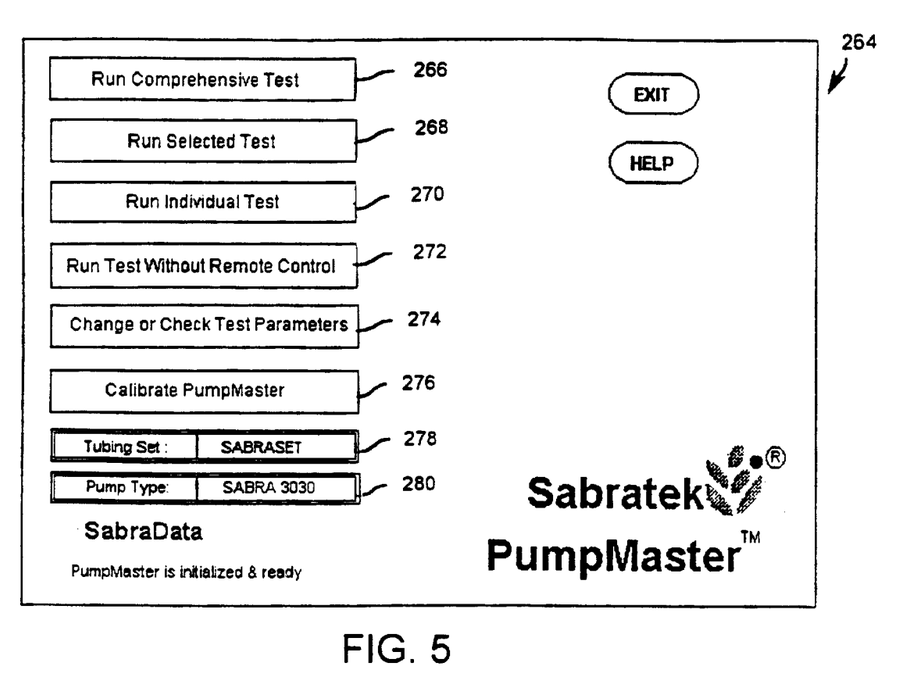
FIGS. 5 and 6 are displays generated during the operation of the pump testing apparatus of FIG. 1.

A flowchart of a main operating routine 260 of a computer program which is executed by the microprocessor 90 of the computer 14 to control the operation of the pump testing apparatus 10 is illustrated in FIG. 4. Referring to FIG. 4, at step 262 a main menu 264 is displayed on the display device 102 of the computer 14. Referring to FIG. 5, the main menu 264 allows the user to select various types of test routines by touching one of a number of selection areas 266–272, to change or check test parameters by touching a selection area 274, to calibrate the testing apparatus 10 by touching a selection area 276, to select a tubing type by touching a selection area 278, and to select a pump type by touching a selection area 280.

Referring to FIG. 4, at step 282 the user selects a pump type, and at step 284 the user selects a tubing type. The testing apparatus 10 may be capable of testing a number of various types of infusion pumps having upstream and downstream tubing portions with different physical characteristics. At step 286, the user selects a number of test parameters via a menu display 288 shown in FIG. 6.

Figure 6:
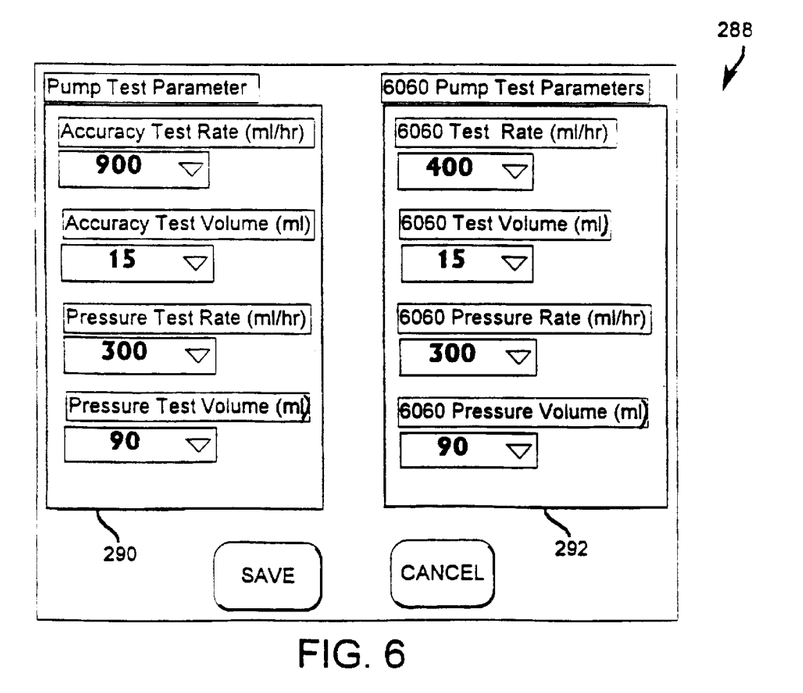

Referring to FIG. 6, the testing apparatus 10 stores one set of test parameters for each of the infusion pumps which it is capable of testing. The test parameters for one pump type are shown in a display area 290 to include a flow rate of 900 ml/hr and a volume of 15 ml for a volume accuracy test (described below) and a flow rate of 300 ml/hr and a volume of 90 ml for a number of occlusion tests (described below). The display area 290 may be initially provided with default test parameters, which can be subsequently changed by the user. A second set of test parameters is shown in a display area 292 for a second type of pump.

Referring back to FIG. 4, if the user wishes to calibrate the testing apparatus 10 (by touching the selection area 276 of FIG. 5) as determined at step 294, the program branches to step 296 where the testing apparatus 10 is calibrated. The calibration procedure, which can be performed in any number of conventional ways, may include placing a calibration element having a known weight (e.g. 10.0 mg) in the container 30 and comparing the known calibration weight with the weight determined by the testing apparatus 10 (based upon the difference between an initial weight reading when the container 30 is empty and a final weight reading when the calibration element is in the container 30). The liquid pressure determined by the pump tester 12 can be calibrated by, for example, providing a known liquid pressure at the downstream conduit 22 and comparing that known pressure with the pressure detected by the pump tester 12 via the pressure transducer 48.

At step 298, the user selects one of a number of test routines by touching one of the selection areas 266–272 of FIG. 5, and at step 300 the test routine selected by the user is performed. The test routines may include a comprehensive test routine that runs all tests which the testing apparatus 10 can perform, a selected test routine that runs a number of specific tests selected by the user, and an individual test routine that runs a single test selected by the user. The user may also run a "Without Remote Control" test which is performed on an infusion pump that requires manual operator intervention to perform the test.

It should be appreciated that the main menu 264 of FIG. 5 allows the user to select the various options in any order by touching the selection areas 266–280. The flowchart of FIG. 4 illustrates one example of the order in which the selection areas 266–280 would be selected by a user where the testing apparatus 10 would be set up (at steps 282–286 of FIG. 4) to sequentially test (at steps 298–300 of FIG. 4) a number of infusion pumps of the same type and having the same tubing characteristics.

Comprehensive Test

Figure 7:
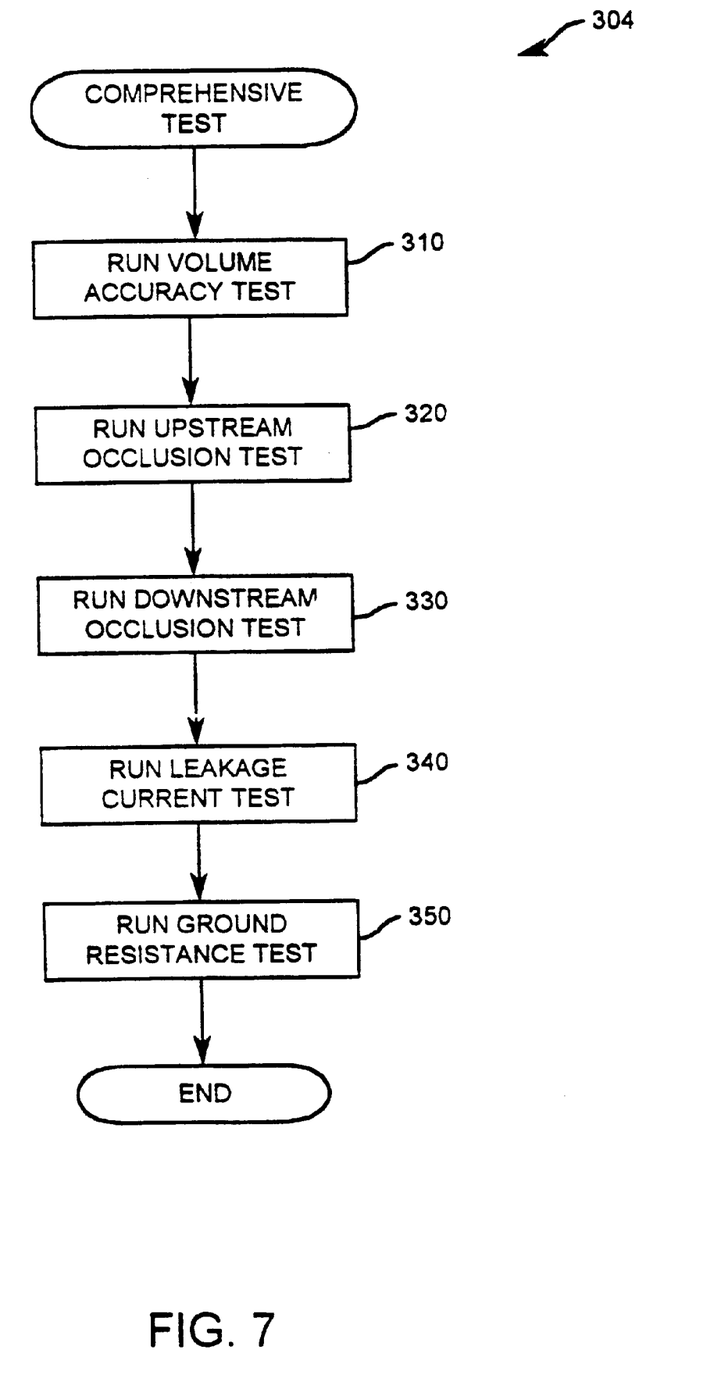
FIG. 7 is an example of a test routine that may be selected by a user of the pump testing apparatus.

FIG. 7 is a flowchart of a comprehensive test routine 304 during which a number of different types of tests are performed on the infusion pump 16, including a volume accuracy test which is run at step 310, an upstream occlusion test which is run at step 320, a downstream occlusion test which is run at step 330, a leakage current test which is run at step 340, and a ground resistance test which is run at step 350. Other tests could also be performed in addition to the above tests, such as a test of the air-in-line sensor 194, a test of the door-open sensor 214, and a test of the bolus-request switch 216.

Volume Accuracy Test

Figure 8:
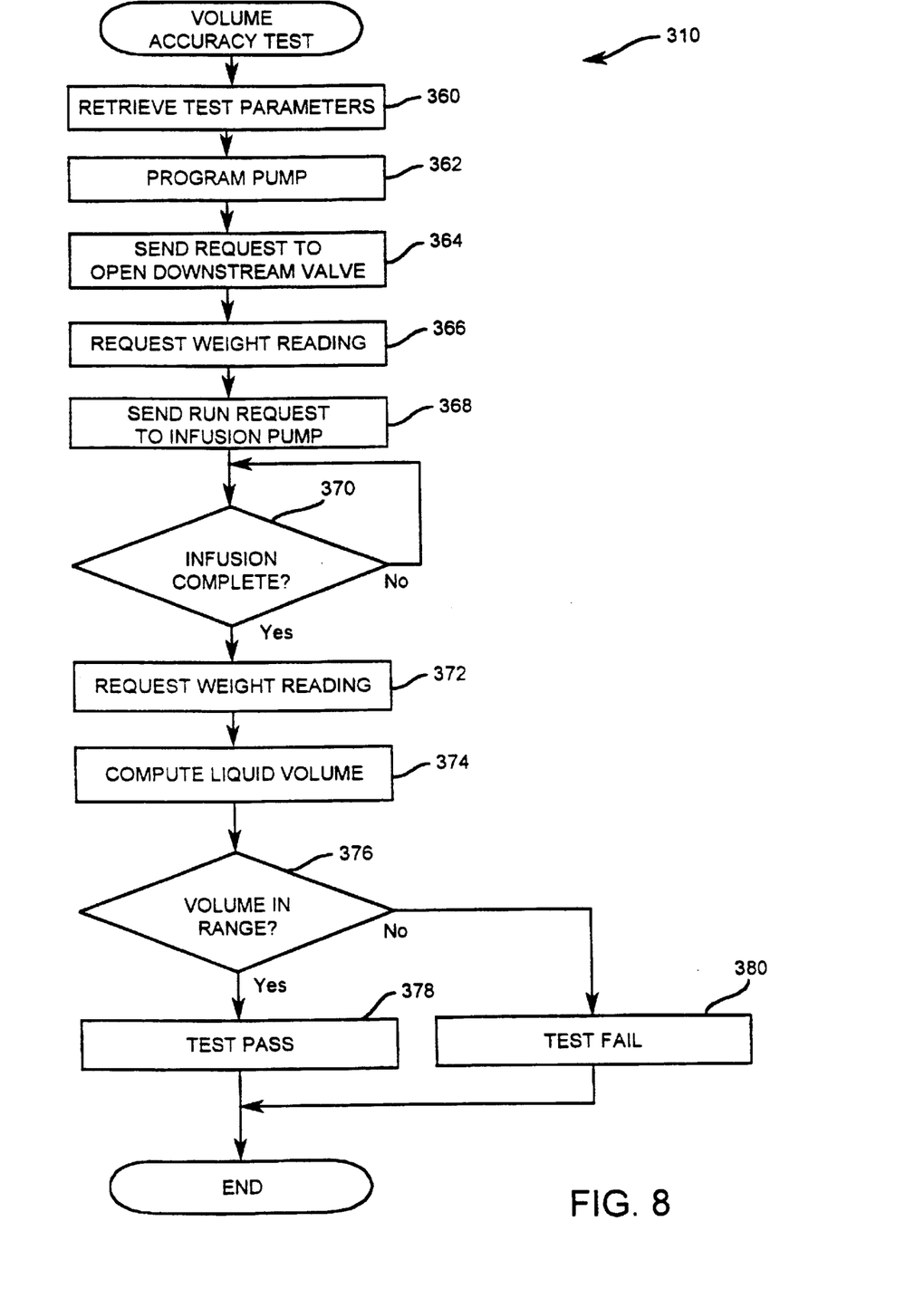
FIG. 8 is a flowchart of the volume accuracy test shown schematically in FIG. 7.

FIG. 8 is a flowchart of the volume accuracy test shown schematically as step 310 in FIG. 7. The volume accuracy test is performed to determine whether the infusion pump 16 delivers the precise liquid volume which it is programmed to deliver.

Referring to FIG. 8, at step 360 the test parameters for the type of infusion pump 16 being tested (the test parameters were selected by the user at step 286 of FIG. 4) are retrieved from memory. For the volume accuracy test, the two test parameters that are used are the flow rate and volume specified in the upper half of one of the display portions 290, 292 of FIG. 6.

At step 362, the infusion pump 16 is programmed by the computer 14. As described above, during normal use the infusion pump 16 is manually programmed by a user via the keypad 110, by selecting the infusion mode, then entering the desired infusion rate and the infusion volume. During step 362, the infusion pump 16 is programmed automatically by the computer 14, by transmitting three electronic programming commands to the infusion pump via the serial communications lines 104, 109. The first electronic programming command specifies the continuous infusion mode (i.e. answers "yes" at step 220 of FIG. 3); the second electronic command specifies the flow rate; and the third electronic command specifies the volume to be infused by the infusion pump 16. These electronic programming commands emulate the electronic signals that would be generated by the keypad 110 if the user had manually pressed it in that the electronic commands generated by the computer 14 include the identical signals that would have been generated by the keypad 110.

The computer 14 knows when to transmit each of these electronic commands to the infusion pump 16 because it can read the display 112 of the infusion pump 16. In particular, upon request by the computer 14, the infusion pump 16 transmits to the computer 14, via the communications lines 104, 109, a sequence of electronic signals, each of which represents a single character currently generated on the display 112. Thus, by continually requesting that the infusion pump 16 transmit the contents of its display 112 via the lines 109, 104, the computer 14 can detect when the display is "Continuous?" (at step 220 of FIG. 3), in which case the computer 14 transmits the electronic command "Y" (meaning yes) to the infusion pump 16 via the communications lines 104, 109.

Because of the ability of the computer 14 to send electronic commands to the infusion pump 16 which emulate the electronic signals that would have been generated by the keypad 110, it is unnecessary for the infusion pump 16 to be manually programmed during the testing procedure.

At step 364, the computer 14 sends a request to the pump tester 12 via the communications lines 104, 108 to open the downstream valve 42 (which is accomplished via the valve control line 76). At step 366, the computer 14 sends a request to the pump tester 12 to take an initial weight reading (via the scale 46) of the container 30 prior to the infusion of any liquid into the container 30 by the infusion pump 16.

At step 368, after the computer 14 detects that the infusion pump display 112 has displayed the rate and volume automatically programmed at step 362, the computer 14 transmits an electronic command to the infusion pump 16, via the communications lines 104, 109, that emulates the "Run" key (which would be manually pressed by a user at step 242 of FIG. 3 during normal operation of the pump 16). Upon receipt of the electronic "Run" command from the computer 14, the infusion pump 16 begins to infuse the volume and flow rate programmed at step 362.

When the infusion is complete as determined at step 370, the program branches to step 372 where the computer 14, via the communications lines 104, 108, requests that the pump tester 12 take a final weight reading of the container 30 and the liquid infused into it by the pump 16. At step 374, the computer 14 determines the liquid volume actually delivered by the infusion pump 16 by subtracting the initial weight reading from the final weight reading, and multiplying the difference by a scale factor (if necessary) to convert the liquid weight to a liquid volume (based on the specific gravity of the liquid used).

At step 376, the actual liquid volume infused by the pump 16 is compared with the liquid volume programmed at step 362. If the actual volume is within a predetermined range of the programmed volume, such as within 5% of the programmed volume, then the program branches to step 378 where the computer 14 records in memory that the pump 16 passed the volume accuracy test. If the actual volume is not within the predetermined range, the program branches to step 380 where the computer 14 records that the pump failed the test.

Upstream Occlusion Test

Figure 9:
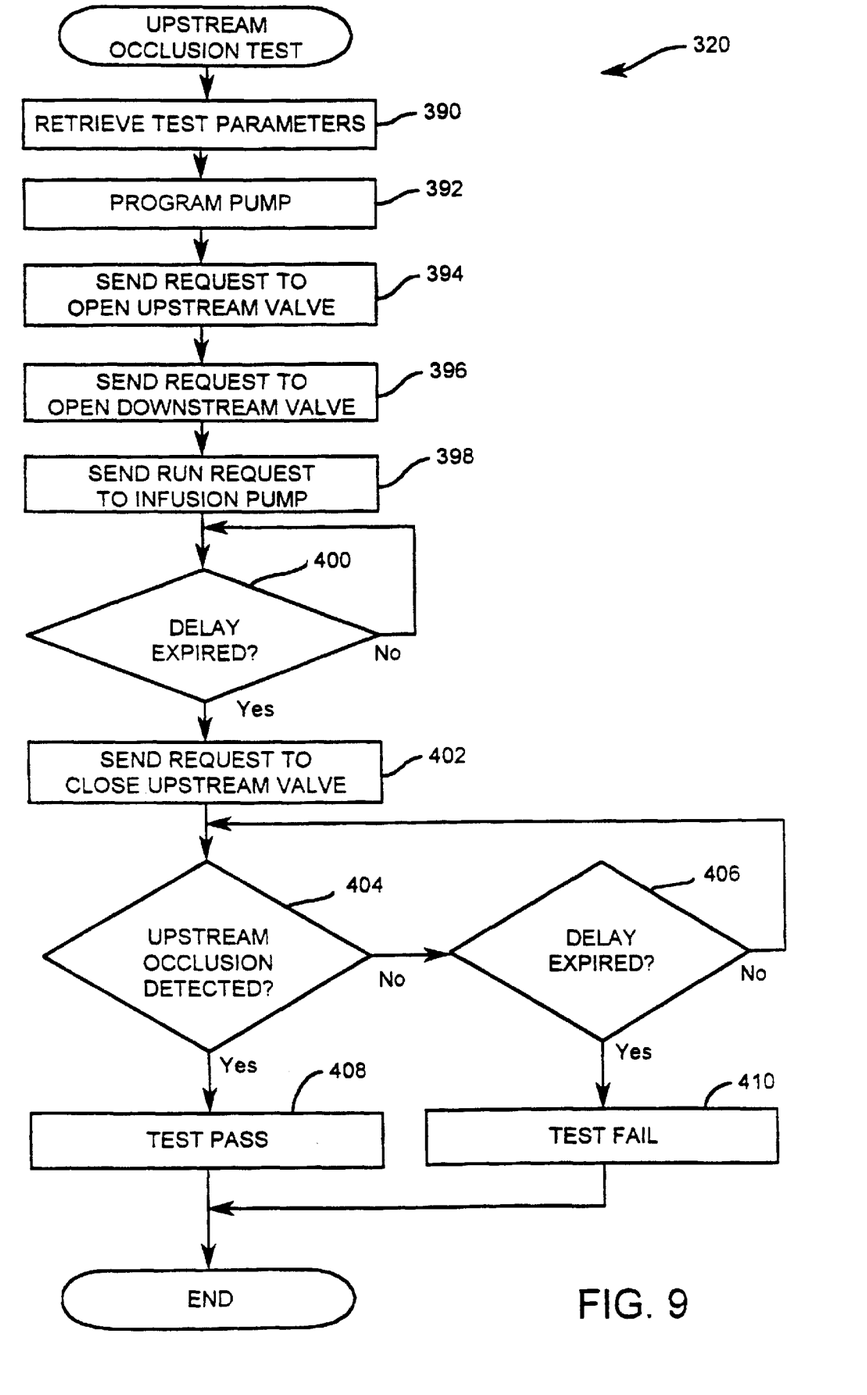
FIG. 9 is a flowchart of the upstream occlusion test shown schematically in FIG. 7.

FIG. 9 is a flowchart of the upstream occlusion test shown schematically as step 320 in FIG. 7. The upstream occlusion test is performed to check whether the input pressure sensor 170 is properly functioning.

Referring to FIG. 9, at step 390 the test parameters for the type of infusion pump 16 being tested (the test parameters were selected by the user at step 286 of FIG. 4) are retrieved from memory. For the upstream occlusion test, the two test parameters that are used are the flow rate and volume specified in the lower half of the display portions 290, 292 of FIG. 6.

At step 392, the computer 14 automatically programs the infusion pump 16 by sending electronic commands specifying the continuous infusion mode and the infusion rate and volume retrieved at step 390, as described above. At step 394, the computer 14 sends a request to the pump tester 12 via the communications lines 104, 108 to open the upstream valve 40 (which is accomplished via the valve control line 72), and at step 396, the computer 14 sends a request to the pump tester 12 to open the downstream valve 42.

At step 398, after the computer 14 detects that the infusion pump display 112 has displayed the rate and volume automatically programmed at step 392, the computer 14 transmits an electronic "Run" command to the infusion pump 16, which causes the infusion pump 16 to begin to infuse the volume and flow rate programmed at step 392.

At step 400, after a predetermined delay, e.g. one minute, the program branches to step 402 where the computer 14 sends a request to the pump tester 12 to close the upstream valve 40. Steps 404 and 406 are repeated until either: 1) the computer 14 detects (by reading the infusion pump display 112) that the infusion pump 16 has generated an upstream occlusion alarm (due to the inlet pressure sensor 170 detecting a low inlet pressure); or 2) a predetermined period, e.g. two minutes, elapses without the detection of an upstream occlusion alarm.

In case 1), the program branches to step 408 where the computer 14 records in memory that the pump 16 passed the upstream-occlusion test. If an upstream occlusion alarm was not detected within the predetermined time limit, the program branches to step 410 where the computer 14 records that the pump failed the test.

Downstream Occlusion Test

Figure 10:
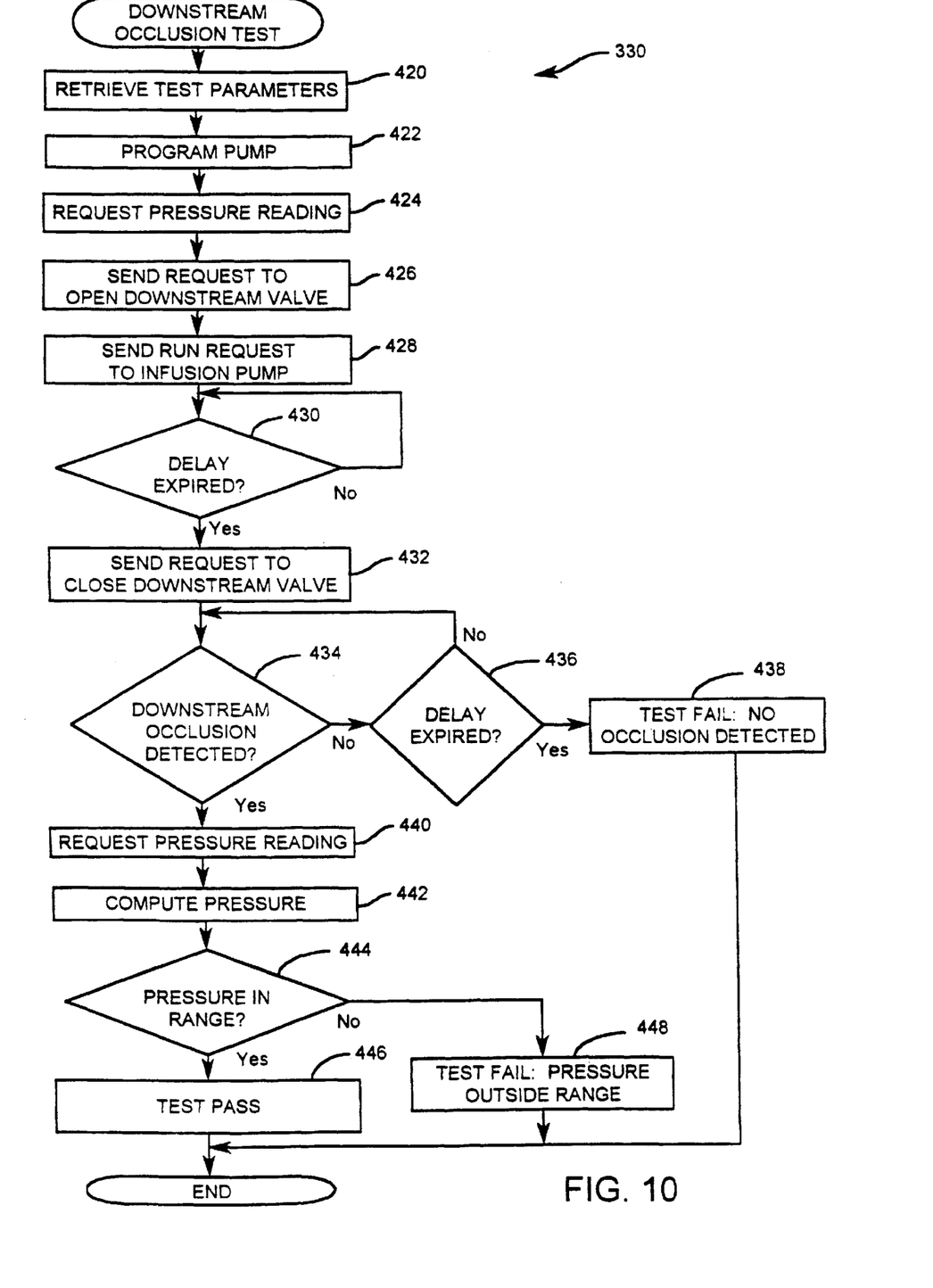
FIG. 10 is a flowchart of the downstream occlusion test shown schematically in FIG. 7.

FIG. 10 is a flowchart of the downstream occlusion test shown schematically as step 330 in FIG. 7. The downstream occlusion test is performed to check whether the output pressure sensor 172 is functioning and whether it is triggered within an acceptable range of pressures.

Referring to FIG. 10, steps 420 and 422 are identical to steps 390 and 392 described above. At step 424, the computer 14 sends a request to the pump tester 12 via the communications lines 104, 108 to take an initial pressure reading via the pressure transducer 48, and step 426, the computer 14 sends a request to the pump tester 12 to open the downstream valve 42.

At step 428, after the computer 14 detects that the infusion pump display 112 has displayed the rate and volume automatically programmed at step 422, the computer 14 transmits an electronic "Run" command to the infusion pump 16, which causes the infusion pump 16 to begin to infuse the volume and flow rate programmed at step 422.

At step 430, after a predetermined delay, e.g. one minute, the program branches to step 432 where the computer 14 sends a request to the pump tester 12 to close the downstream valve 42. Steps 434 and 436 are analogous to steps 404 and 406 described above. If the computer 14 does not detect that the infusion pump 16 generated a downstream occlusion alarm on its display 112 within a predetermined period of time, the program branches to step 438 where the computer 14 records in memory that the pump 16 failed to generate a downstream occlusion alarm.

At step 434, upon the detection that the infusion pump 16 generated a downstream occlusion alarm within the time limit, the program branches to step 440 where the computer 14 sends a request to the pump tester 12 to take a final pressure reading from the pressure transducer 48. At step 442, the computer 14 determines the difference between the two pressure readings and then at step 444 determines whether that difference is within a predetermined range. If the difference is in range, the program branches to step 446 where the computer 14 records that the pump passed the test.

Otherwise, the program branches to step 448 where the computer 14 records that the pump 16 failed the test since the pressure at which the downstream occlusion alarm was generated was not within a range of acceptable pressures (the acceptable pressure range may depend on whether the infusion pump 16 is used for venous infusion, e.g. 8+/−5 psi, or arterial infusion, e.g. 20+/−5 psi).

Electrical Tests

Figure 11:
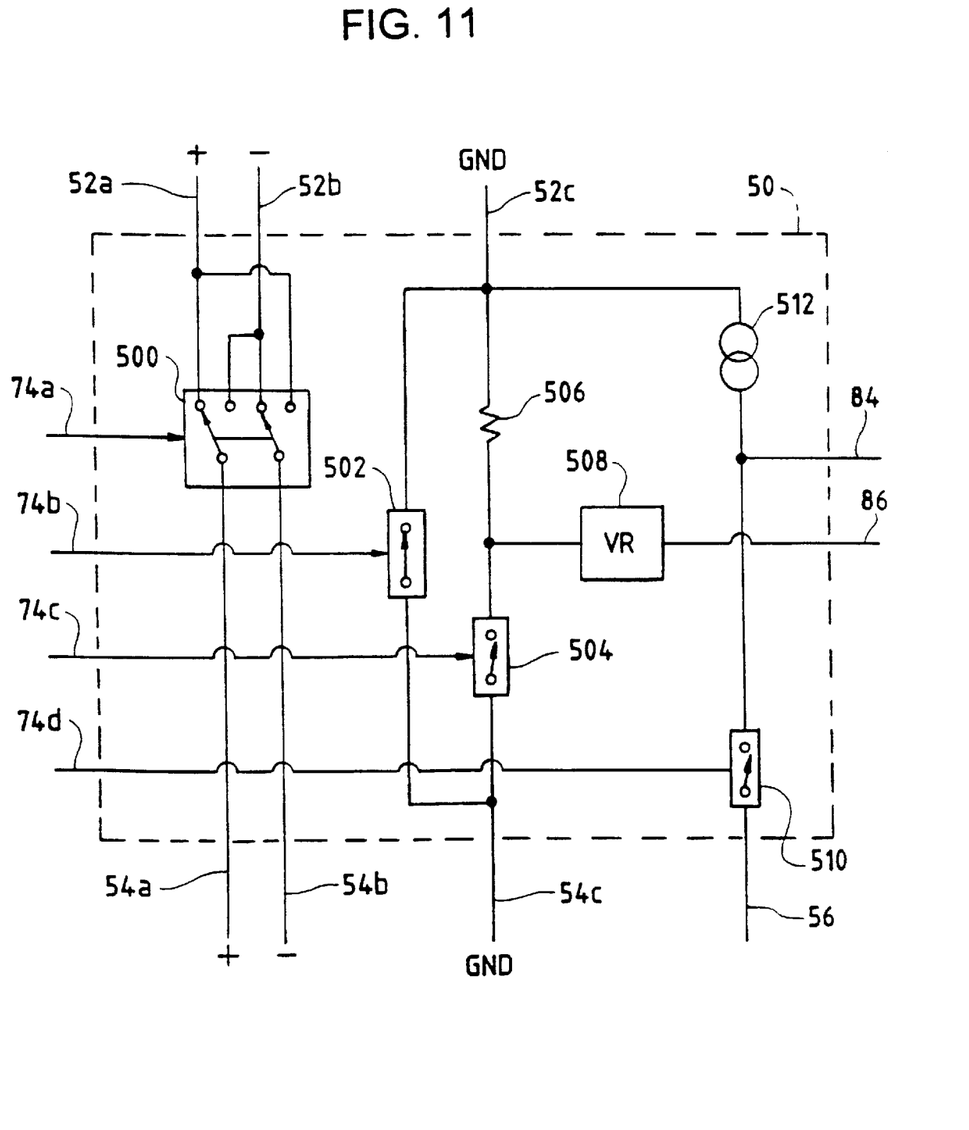
FIG. 11 is a circuit diagram of the test circuit shown schematically in FIG. 1.

FIG. 11 illustrates a circuit diagram of the electrical test circuit 50 schematically shown in FIG. 1. Referring to FIG. 11, the test circuit 50 includes a double pole, double throw switch 500 connected between the high and low power lines 52a, 52b, 54a, 54b. The switch 500 is shown in its normally deenergized state. When energized via the control line 74a, the switch 500 reverses the polarity on the power lines 54a, 54b by connecting the line 52a to the line 54b and the line 52b to the line 54a.

The test circuit 50 has a switch 502 shown in its normally deenergized state which connects the ground line 52c to the ground line 54c connected to the infusion pump 16. The circuit 50 has a switch 504 shown in its normally deenergized state which, when energized, connects the ground line 52c to the ground line 54c through an impedance circuit (which may consist of a conventional bridge circuit having two legs with a resistor in each leg and a third leg having a resistor and a capacitor) schematically shown at 506. A voltage rectifier (VR) 508, which is connected to the junction of the switch 504 and the impedance circuit 506, generates a rectified voltage signal which is transmitted to the A/D converter 68 via the line 86.

The test circuit 50 has a switch 510 shown in its normally deenergized state which, when energized, connects the ground line 52c to the separate ground line 56. A constant current source 512 is connected between the line 52c and the switch 510, and the line 84 to the A/D converter 68 is connected to the junction of the current source 512 and the switch 510.

When the leakage current test is run at step 340 of FIG. 7, with the switch 500 in its position shown in FIG. 11, the switch 502 is opened and the switch 504 is closed (the switch 510 remains open) so that any leakage current that passes from the infusion pump via the ground line 54c generates an AC voltage across the impedance 506, which voltage is rectified by the rectifier 508. The magnitude of the voltage, and thus the leakage current, is measured by the A/D converter 68. Then, the switch 500 is switched (the other switches are not changed), and the leakage current is again measured by detecting the magnitude of the voltage on the line 86. The larger of the two voltages measured by the A/D converter 68 may be compared against a voltage threshold to determine whether the leakage current level is acceptable. If the leakage current is below an acceptable level, the computer 14 records that the infusion pump 16 passed the leakage current test.

The ground resistance of the infusion pump 16 is the resistance between the ground line 54c of the power cord and the separate ground line 56. Prior to running the ground resistance test, the pump tester 12 may be calibrated based on a known ground resistance. When the ground resistance test is run at step 350 of FIG. 7, the switches 502 and 510 are closed and the switch 504 is opened, and the constant current source 512 supplies a known current to the infusion pump 16 via the ground line 56. Any resistance between the power ground line 54c and the ground line 56 causes a voltage to be generated on the line 84, which is measured by the A/D converter 68. If the ground resistance is below an acceptable level, the computer 14 records that the infusion pump 16 passed the ground resistance test.

The electrical tests, and the other tests described above, may not be applicable to all infusion pumps which may be tested by the testing apparatus 10. For example, where the testing apparatus 10 is capable of testing two different types of infusion pumps, some tests may not be capable of being performed on both types of pumps.

Pump Recertification Record

Figure 12:
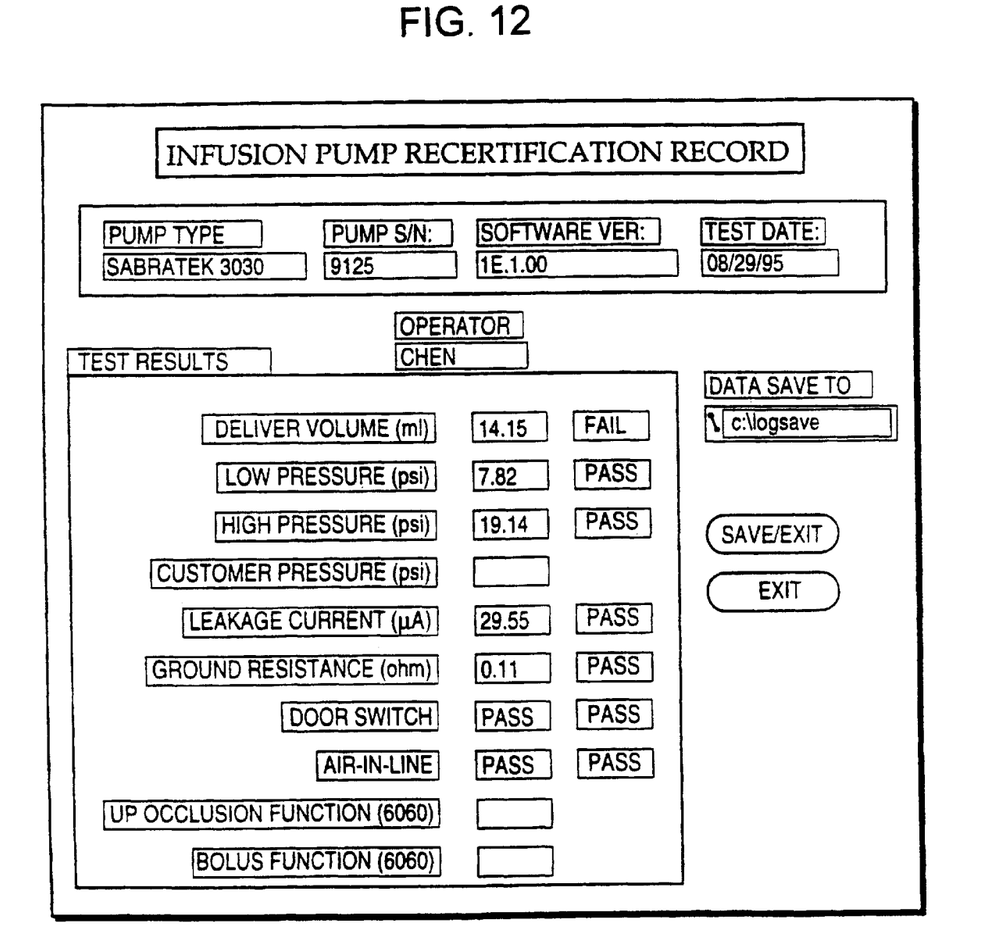
FIG. 12 is a testing record which may be generated by the pump testing apparatus of FIG. 1.

Based on the results of the tests performed on the infusion pump 16, the computer 14 may generate a written record of the test results. One example of such a written record is illustrated in FIG. 12.

Modifications and alternative embodiments of the invention will be apparent to those skilled in the art in view of the foregoing description. This description is to be construed as illustrative only, and is for the purpose of teaching those skilled in the art the best mode of carrying out the invention. The details of the structure and method may be varied substantially without departing from the spirit of the invention, and the exclusive use of all modifications which come within the scope of the appended claims is reserved.

What is claimed is:

1. An apparatus for automatically testing an infusion pump operable in an operation sequence for pumping a liquid through a conduit, said apparatus comprising:

a pump tester adapted to be coupled to said infusion pump, said pump tester comprising:
volume accuracy means for performing a volume accuracy test;
upstream occlusion means for performing an upstream occlusion test; and
downstream occlusion means for performing a downstream occlusion test; and means for automatically causing said infusion pump to undergo said operation sequence without manual activation of said infusion pump by a user comprising:
program means for generating a plurality of testing commands;
a communications link to the infusion pump for receiving said testing commands; and
signal transmission means for transmitting said testing commands to said infusion Dump via said communications link;

said pump tester performing a series of tests and said infusion pump being operated in accordance with the series of tests performed by said pump tester for determining the volume accuracy of the liquid being pumped through the conduit by the infusion pump with said volume accuracy means, creating an upstream occlusion in the conduit for observing an upstream occlusion alarm by the infusion pump with said upstream occlusion means, and creating a downstream occlusion in the conduit for observing a downstream occlusion alarm by the infusion pump with said downstream occlusion means;

a pressure sensor for generating a signal relating to the pressure of said liquid within said conduit;

means for determining whether said infusion pump generates a downstream occlusion signal in response to an interruption of liquid flow through said conduit; and wherein said pump tester has a second conduit, said second conduit being adapted to provide liquid to said infusion pump from a liquid source and wherein said means for performing said upstream occlusion test comprises:

a valve coupled to said second conduit for selectively interrupting the flow of said liquid through said second conduit; and means for determining whether said infusion pump generates an upstream occlusion signal in response to an interruption of liquid flow through said second conduit.

2. An apparatus as defined in claim 1 wherein said means for performing said volume accuracy test comprises:

a container into which a quantity of liquid is pumped during said operation sequence of said infusion pump; and means for determining the volume of said quantity of liquid.

3. An apparatus as defined in claim 1 wherein said means for performing said downstream occlusion test additionally comprises means for determining whether said liquid pressure is within a given range upon the detection of a downstream occlusion by said infusion pump.

* * * * *

UNITED STATES PATENT AND TRADEMARK OFFICE
CERTIFICATE OF CORRECTION

PATENT NO. : 5,943,633
DATED      : August 24, 1999
INVENTOR(S): Larry WILSON et al.

It is certified that error appears in the above-identified patent and that said Letters Patent is hereby corrected as shown below:

Column 11, line 41, change "Dump" to --pump--.

Signed and Sealed this

Twenty-ninth Day of February, 2000

Attest:

Q. TODD DICKINSON

*Attesting Officer*    *Commissioner of Patents and Trademarks*